United States Patent [19]

Tritsch

[11] 4,044,767
[45] Aug. 30, 1977

[54] TAB FASTENER HAVING TWO TAPE SEGMENTS ATTACHED TO EACH OTHER AND TO DIAPER

[75] Inventor: Ludwig Tritsch, Wilmette, Ill.

[73] Assignee: Johnson & Johnson, New Brunswick, N.J.

[21] Appl. No.: 661,919

[22] Filed: Feb. 27, 1976

[51] Int. Cl.² .......................................... A61F 13/16
[52] U.S. Cl. .................................................. 128/287
[58] Field of Search .............. 128/287, 284, 286, 290; 24/67 AR, DIG. 11

[56] References Cited

U.S. PATENT DOCUMENTS

| | | | |
|---|---|---|---|
| 3,776,234 | 12/1973 | Hoey | 128/287 |
| 3,848,594 | 11/1974 | Buell | 128/287 |
| 3,875,621 | 4/1975 | Karami | 128/287 X |
| 3,880,165 | 9/1975 | Prizzia | 128/287 X |

*Primary Examiner*—Stephen C. Pellegrino

[57] ABSTRACT

A disposable diaper has an improved tape tab fastening means comprising a securing tape segment and a backing web associated therewith. The backing web has a first leg attached to the diaper backing sheet and a second leg attached to the diaper facing sheet. The securing tape segment has a fixed end attached directly to the diaper backing sheet inwardly of the first leg, an intermediate portion attached to the first leg, and an adhesive-coated free end releasably attached to the second leg. The free end is separable from the second leg to make the free end available for securing the diaper about an infant. Stresses imposed on the securing tape segment when in use are distributed to both the diaper facing sheet and the diaper backing sheet via the intermediate portion and fixed end of the tape segment. In another embodiment, a transferable tape ribbon is releasably attached to the free end to enable an applied diaper to be opened or removed from the infant and thereafter to be refastened about the infant. In a further embodiment, pre-assembled tab fasteners are provided for securing together two flaps, such as opposite corners of a disposable diaper.

17 Claims, 10 Drawing Figures

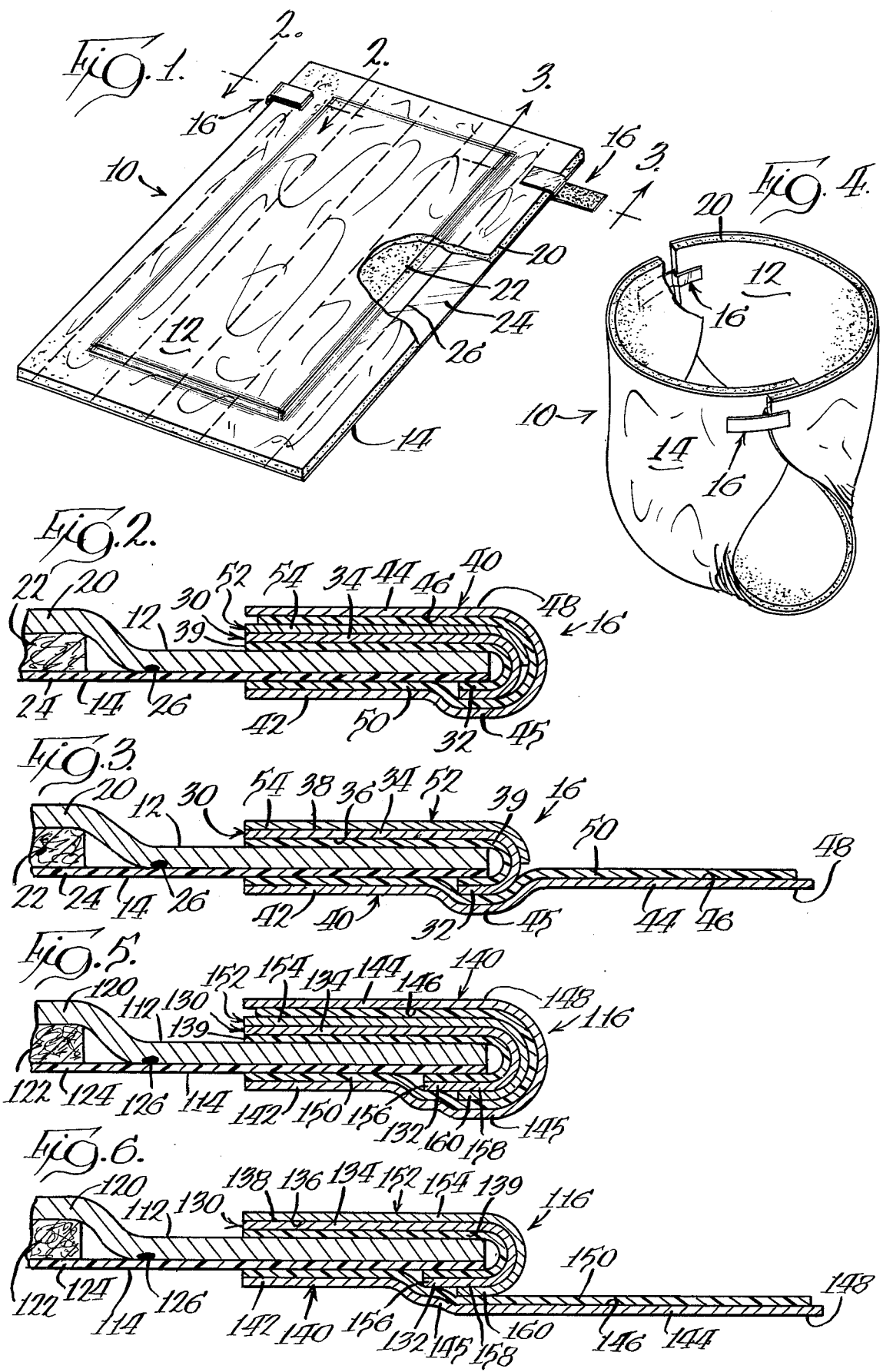

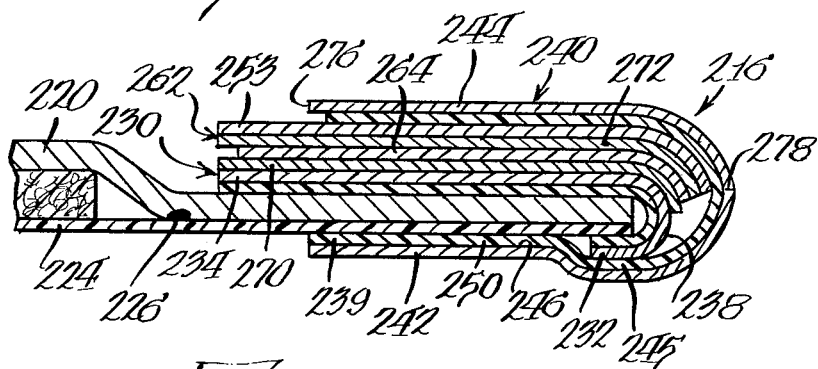
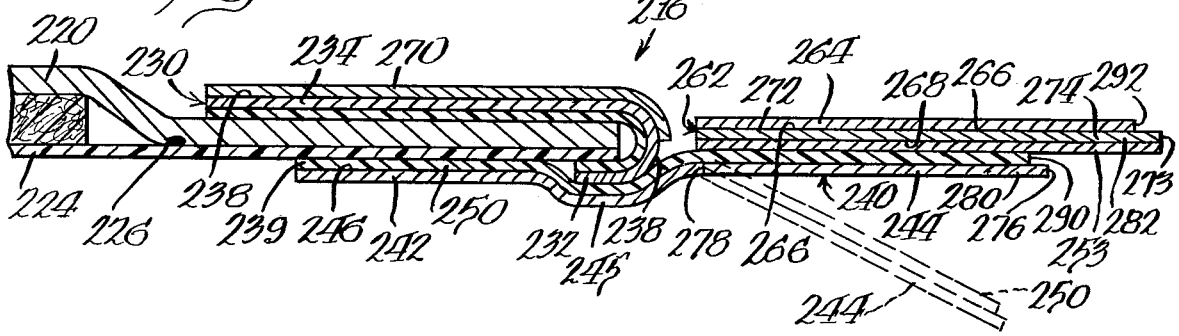
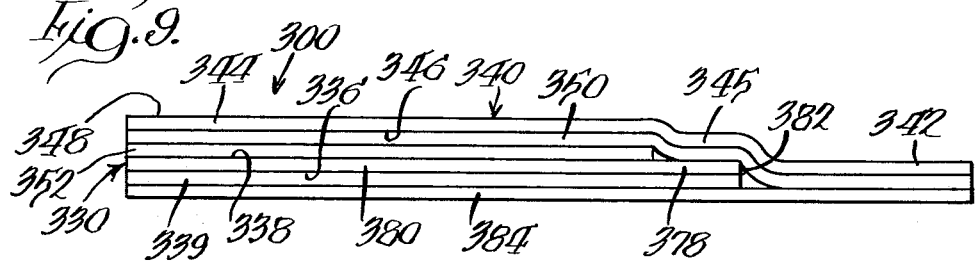
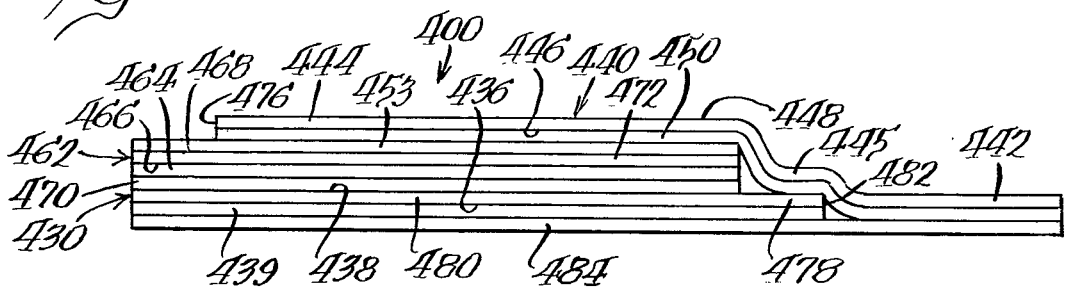

TAB FASTENER HAVING TWO TAPE SEGMENTS ATTACHED TO EACH OTHER AND TO DIAPER

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,646,937 to Gellert teaches a fastening tab which is provided with a release surface permanently bonded primarily to the inside surface of the diaper. One of the drawbacks of the Gellert arrangement is that in use the adhesive tape fasteners are permanently attached to only one surface of the diaper, generally the outside surface of the backing sheet, and thus the bond between one end of the tape fastener and the diaper backing sheet is subjected to all of the stresses exerted on the tape fastener during securement or as the infant moves about.

U.S. Pat. No. 3,750,669 to DeLuca shows a fastening tape provided with an adhesive end portion which extends beyond a cover strip for the tape and which is attached to a diaper inner covering or facing. However, such an adhesive end portion, when attached to a fibrous, non-woven facing fabric, may tear the facing fabric upon separation therefrom.

U.S. Pat. No. 3,776,234 to Hoey proposes to fold the tab over on itself at the diaper's edge and to adhesively attach a portion of the folded-over tab segment to an inwardly folded margin of the diaper backing sheet in order to keep the tab flat against the diaper and thus from interfering with the manufacturing machinery and with the subsequent folding and packaging operations. This requires that the edge of the diaper backing sheet be folded over to present an attachment surface at the front or inside face of the diaper, and a relatively involved tab design is necessary for this purpose. Also, undesirable tearing of the diaper facing fabric may result if such a tab is inadvertently adhesively attached to the facing fabric of the diaper during manufacture.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two interconnected tape portions which cause the folded configuration of the sealing tape to be somewhat bulky.

The adhesive fastener disclosed in U.S. Pat. No. 3,833,456 to Reed et al. can also be attached to both the front and back surfaces of a diaper to provide for force distribution over both surfaces. This particular fastener comprises two co-extensive webs with each web having an adhesive coating extending along substantially all of one face. The lower or base web also has a release coating on one end portion of its opposite face so that a portion of the adhesive coating on the upper web is releasably secured thereto while the rest of the adhesive coating on the upper web bonds the two webs together. Since two substantially co-extensive webs are present, the fastener is bulky in the folded configuration, and is relatively expensive to manufacture.

A similar tape fastener is shown in U.S. Pat. No. 3,848,594 to Buell wherein the tape fastener is also attached to both the front and back surfaces of the diaper while having a securing portion attached to an adjacent section of the diaper. Such a construction takes away from the adhesive area that is available on the free tab end for diaper securement. It also has the disadvantage in that each tape fastener is comprised of two or more separate tape segments which are joined together so as to produce a common area of joinder for both fastener anchoring legs and the fastener securing portion and thereby adding complexities and expense to the manufacturing process, as well as requiring careful positioning during diaper manufacture.

SUMMARY OF THE INVENTION

According to the present invention, an improved economical tape tab fastener system for use in disposable diapers permits the distribution of stresses which are imposed on the tape tab to both the diaper facing sheet and the diaper backing sheet.

The tab includes a backing web which is folded about the edge of the diaper and a securing tape segment. The backing web comprises a backing leg attached to the backing sheet and a facing leg attached to the facing sheet. Preferably, the facing leg is longer than the backing leg so that the backing web assumes a generally J-shaped configuration when the tab is affixed to a diaper. The securing tape segment has a fixed end attached directly to the backing sheet inwardly of the backing leg, an intermediate portion attached to the backing leg, and a free working end which is provided with a pressure-sensitive adhesive coating and is releasably attached to the facing leg. To secure the diaper about an infant, the free end can be separated from the facing leg, and stresses imposed on the free end are distributed to both the facing sheet and backing sheet via the fixed end and the intermediate portion of the tape segment.

According to another embodiment, the applied diaper can be opened and reclosed without tearing the tape tab and without rupturing the diaper by means of a transferable tape ribbon which has one face releasably attached to the facing leg and an opposite face which is releasably attached to the free working end of the securing tape segment. The transferable tape ribbon is separable from the facing leg to initially secure the diaper about an infant while still connected to the securing tape segment. To remove the diaper from the infant, the free working end of the securing tape segment is separated from the transferable tape ribbon, which remains attached to the diaper backing sheet whereby the adhesive coating on the free end is exposed and is available for use in refastening the diaper about the infant.

The tape tabs of the present inention can be used for securing together two flaps, such as opposite corners of a disposable diaper, and can be pre-assembled and thereafter positioned on the diaper.

The improved tape tab system of the present invention enables stresses imposed on the tape tab to be distributed to both the facing sheet and the backing sheet of the diaper, thereby minimizing the possibility of undesirable rupture of the diaper when in use. Additionally, one of the embodiments of this invention allows someone inspecting or adjusting the diaper to open and reclose the tape tap closure during the service of the diaper, thereby providing the economical advantage of inspection and repositioning of the diaper until soiled. Upon refastening, the tape tab fasteners of this invention provide a good, strong securement to the diaper. Further features are economy of manufacture, a built-in release means which obviates the need for a removable cover strip, and a pre-assembled tape tab which can be applied to the diaper.

BRIEF DESCRIPTION OF THE DRAWINGS

FIG. 1 is a perspective view, partially broken away to show interior detail, of an open unfolded diaper n accordance with the present invention;

FIG. 2 is an enlarged fragmentary cross-sectional view of the diaper of FIG. 1 taken along plane 2—2;

FIG. 3 is an enlarged fragmentary cross-secctional view of the diaper of FIG. 1 taken along plane 3—3;

FIG. 4 is a perspective view of the diaper of FIG. 1 in a configuration assumed by the diaper when placed about an infant;

FIG. 5 is a fragmentary cross-sectional view similar to FIG. 2 and showing another embodiment of the invention;

FIG. 6 is a fragmentary cross-sectional view showing the embodiment of FIG. 5 in the extended working position;

FIG. 7 is a fragmentary cross-sectional view similar to FIGS. 2 and 5 and showing yet another embodiment of the invention;

FIG. 8 is a fragmentary cross-sectional view showing the embodiment of FIG. 7 in the extended working position, and showing in phantom the position which can be assumed by the detachable portion of the tab fastener;

FIG. 9 is a cross-sectional view illustrating a preassembled tab fastener embodying the present invention; and FIG. 10 is a cross-sectional view illustrating another pre-assembled tab fastener in accordance with the present invention.

DESCRIPTION OF THE PREFERRED EMBODIMENTS

In the following description, two digit numerals are used to refer to the embodiment illustrated in FIGS. 1–4, three digit numerals in the one hundred series are used to refer to the embodiment illustrated in FIGS. 5 and 6, three digit numerals in the two hundred series are used to refer to the embodiment illustrated in FIGS. 7 and 8, three digit numerals in the three hundred series are used to refer to the embodiment illustrated in FIG. 9 and three digit numerals in the four hundred series are used to refer to the embodiment illustrated in FIG. 10. The same last two digits in each numeral designate similar elements in the various embodiments.

Disposable diaper 10, illustrated in FIGS. 1 and 4, is of substantially quadrilateral configuration and presents inside surface 12 for direction toward an infant and outside surface 14 for direction away from the infant. Adhesive tab fastener means such as tabs 16 are attached to diaper 10 for securing diaper 10 about an infant. As described in greater detail below, tabs 16 are movable from a folded-over storage position illustrated in FIG. 2 to an extended working position which is illustrated in FIG. 3.

Referring to FIGS. 1–3, diaper 10 comprises moisture-pervious facing sheet 20, defining diaper inside surface 12 and overlying moisture-retaining absorbent pad 22, and backing sheet 24 which is made of a moisture-impervious material and defines diaper outside surface 14. Absorbent pad 22 is somewhat smaller than backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to the backing sheet 24 by means of adhesive beads 26, glue spots, or in any other convenient manner. For example, if backing sheet 24 is made of a thermoplastic material, facing sheet 20 and pad 22 can be attached thereto by heat bonding, or similar means.

As illustrated in FIGS. 2 and 3, adhesive tab 16 includes backing web 30 which is folded over about the longitudinal edge of the diaper to form a pair of anchoring legs comprising backing anchoring leg 32 and facing anchoring leg 34, each having inner face 36 and outer face 38. Anchoring legs 32 and 34 receive a marginal portion of the diaper therebetween, and are provided with an adhesive coating which may comprise a continuous adhesive coating 39 on the inner face 36 thereof. Facing anchoring leg 34 is permanently attached to a marginal portion of facing sheet 20 and backing anchoring leg 32 is permanently attached to a marginal portion of backing sheet 24 by means of adhesive coating 39 which is substantially coextensive with both anchoring legs 32 and 34. Preferably, backing web 30 assumes a generally J-shaped configuration when attached to the diaper. Adhesive coating 39 can be a pressure-sensitive adhesive composition, a heat-activated or solvent-activated adhesive composition, or the like.

Tab 16 further includes securing tape segment 40 having fixed end 42, free working end 44, and intermediate portion 45 therebetween, each having an inner face 46 and an outer face 48. Fixed end 42, free end 44 and intermediate portion 45 are all provided with adhesive coatings which may comprise a continuous pressure-sensitive adhesive coating 50 on inner face 46 thereof. By means of adhesive coating 50, fixed end 42 is permanently attached to backing sheet 24 inwardly of backing anchoring leg 32, and intermediate portion 45 is permanently attached to outer face 38 of backing anchoring leg 32. Pressure-sensitive adhesive coating 50 on free end 44 faces in the same direction as diaper inside surface 12 when tab 16 is in the working position, and provides a securement means which can be moved from the closed, storage position of FIG. 2 to the extended, working position of FIG. 3 for fastening the diaper about an infant. Since tape segment 40 is secured both to backing sheet 24 and backing web 30, and since the backing web is permanently attached both to facing sheet 20 and backing sheet 24, stresses imposed on free end 44 of securing tape segment 40 are distributed both to backing sheet 24 and facing sheet 20, especially after backing sheet 24 has begun to stretch under load, thereby minimizing the possibility of undesirable rupture of the diaper components.

Release means 52 is associated with backing web 30 and is adapted to be releasably attached to adhesive coating 50 on free end 44. Preferably, release means 52 is a coating carried on outer face 38 of backing web 30. Free end 44 of tape segment 40 is movable from a folded-over storage position in which free end 44 is releasably adhered to release means 52, to a working position in which pressure-sensitive adhesive coating 50 on free end 44 is available for use in securing the diaper about an infant.

Facing anchoring leg 34 is desirably longer than backing anchoring leg 32. In the embodiment illustrated in FIGS. 2 and 3, release means 52 includes release-carrying web 54 on outer face 38 of facing anchoring leg 34 which provides a release region substantially coextensive with pressure-sensitive adhesive coating 50 on free end 44 of securing tape segment 40. Backing anchoring leg 32 is not of substantial length and provides a zone of permanent attachment between backing web 30 and securing tape segment 40.

The embodiment depicted in FIGS. 5 and 6 is similar to the embodiment shown in FIGS. 2 and 3, except that backing anchoring leg 132 includes a distal end segment 156 and an opposite end segment 158 situated between facing anchoring leg 134 and distal end segment 156. Release means 152 includes first release portion 154 on outer face 138 of facing anchoring leg 134 and second release portion 160 on outer face 138 of opposite end segment 158 of backing anchoring leg 132. Securing tape segment 140 has fixed end 142 permanently attached to backing sheet 124 inwardly of backing anchoring leg 132, and intermediate portion 145 is permanently attached to distal end segment 156 of first anchoring leg 132. Thus, release means 152 extends along at least a portion of both anchoring legs 132 and 134, and distal end segment 156 need not be of substantial length to provide a zone of permanent attachment between backing web 130 and tape segment 140.

In both of the above-described embodiments, that portion of backing anchoring legs 32, 132 which is adhesively attached to tape segment 40, 140 can be about ¼ inch to about ⅜ inch in length or longer, to provide the desired zone of attachment.

Referring now to the embodiment illustrated in FIGS. 7 and 8, repositionable tab fastener 216 includes backing web 230 having backing anchoring leg 232 permanently attached to backing sheet 224, and facing anchoring leg 234 permanently attached to facing sheet 220. Tape segment 240 has fixed end 242 permanently attached to backing sheet 224 inwardly of backing anchoring leg 232, free end 244, and intermediate portion 245 which is permanently attached to outer face 238 of backing anchoring leg 232 by means of pressure-sensitive adhesive coating 250 on inner face 246 of tape segment 240.

Tab 216 further includes transferable tape ribbon 262 having pressure-sensitive adhesive coating 264 on inner face 266, and an outer face 268 which can carry release coating 253 in order to provide removable attachment to free end 244 of tape segment 240. Depending on the tab materials used, in some instances a release means is not needed for this purpose inasmuch as outer face 268 can inherently possess adequate release properties. In other instances only a partial release coating may be needed. A release means such as release coating 270 is provided on facing anchoring leg 234 for engagement with pressure-sensitive coating 264 on transferable tape ribbon 262, the transferable tape ribbon being separable from release coating 270 to make the pressure-sensitive adhesive coating 264 available for us ein securing the diaper about an infant. Release coating 270 includes a release portion on outer face 238 of facing anchoring leg 234 which provides a release region substantially coextensive with pressure-sensitive adhesive coating 264 on transferable tape ribbon 262.

Transferable tape ribbon 262 coacts with tape segment 240 and provides securement means for initially fastening the diaper about an infant. Tape segment 240 and transferable tape ribbon 262 are folded about the longitudinal edge of the diaper to assume the folded-over, storage position shown in FIG. 7 in which adhesive coating 264 is releasably adhered to second release coating 270 and can be moved to the extended, working position shown in FIG. 8 in which the adhesive coating 264 is available for use in securing the diaper about an infant. Adhesive coating 264 faces in the same direction as diaper inside surface 212 when transferable tape ribbon 262 is in the working position.

Thus, when tab 216 is in the extended working position of FIG. 8, fixed end 242 of tape segment 240 is attached to one corner of the diaper, and free working end 244 of tape segment 240 is adapted to secure the diaper about an infant by adhesive attachment to the outside surface 214 of the opposite corner of the diaper via the transferable tape ribbon 262 which is carried entirely by free working end 244. Free working end 244 of tape segment 240 is removable from transferable tape ribbon 262 to enable the diaper to be opened or removed from the infant, and to make adhesive coating 250 on free working end 244 of tape segment 240 available for use in refastening the diaper about an infant. A release means such as release coating 253 can be provided on tape ribbon 262 for this purpose, however the removable attachment of free working end 244 to tape ribbon 262 is stronger than the releasable attachment of tape ribbon 262 to release coating 270 in order to provide the desired securement of the applied diaper before tape ribbon 262 and free working end 244 are separated from one another. Free working end 244 of tape segment 240 is made detachable from and refastenable to transferable tape ribbon 262 for inspecting and/or repositioning the diaper about an infant, and is movable from the extended working position illustrated in solid lines in FIG. 8 wherein free working end 244 is adhesively attached to transferable tape ribbon 262, to the detached position illustrated in phantom wherein free working end 244 is separated from transferable tape ribbon 262 which remains fastened to the diaper. When the diaper is in the fastened condition, a portion of the transferable tape ribbon 262 lies between tape segment 240 and diaper outside surface 214.

To avoid undesirable premature adhesion of diaper backing sheet to tab segment 240, preferably transferable tape ribbon 262 is positioned so as to minimize the gap between ribbon 262 and the curved-around portion of anchoring leg 234. Alternatively, the adhesive mass on tape segment 240 which is exposed through the gap can be covered up in any convenient manner, or removed to provide a non-adhesive zone, or zone-coated.

Tape segment 240 can be peeled from transferable tape ribbon 262 without disturbing the adhesive attachment of transferable tape ribbon 262 to diaper outside surface 214. This can be accomplished because tape segment 240 is adhesively but removably attached to only a portion of transferable tape ribbon 262, i.e., the fixed portion 272 which is coextensive with free end 244, so that stresses imposed on transferable tape ribbon 262 when tape segment 240 is separated therefrom are imposed at a location spaced from the outermost edge 273 of transferable tape ribbon 262 which remains attached to the diaper. The grippable portion 274 extends beyond edge 276 of tape segment 240, and preferably has a length at least as great as the width of transferable tape ribbon 262 to facilitate separation of tape segment 240 from transferable tape ribbon 262. Transferable tape ribbon 262 acts as a reinforcing agent by remaining on the diaper where the original closure was made and adds strength to the area of the diaper which might otherwise tear upon peeling of tape segment 240 from transferable tape ribbon 262 due to the stresses imposed on the diaper by the peeling action.

When diaper inspection and/or adjustment is completed, the diaper is wrapped around the infant as was done originally and is refastened by positioning tape segment 240 in an overlapping relationship with transferable tape ribbon 262 which remains attached to the opposite corner of the diaper. Adhesive coating 250 on free working end 244 is pressed against outer face 268 of transferable tape ribbon 262 to complete the closure. Since an overlapping relationship of a portion of tape segment 240 and transferable tape ribbon 262, or the attachment of tape segment 240 directly to diaper backing sheet 224, will furnish a sufficient adhesive closure, there need not be a complete registry between tape segment 240 and transferable tape ribbon 262 upon subsequent refastenings. Thus, a looser fit around the infant can be attained by overlapping only a portion of free working end 244 with transferable tape ribbon 262 or by securement without any overlap at all. Since transferable tape ribbon 262 is longer than free working end 244 of segment 240, the fit of the diaper can be tightened by overlapping free working end 244 with at least a portion of grippable portion 274 of transferable tape ribbon 262. Of course, when free working end 244 is adhesively attached directly to backing sheet 224, additional detachments and refastenings of the diaper will not be possible, and in this case, a line of weakening 278 may be provided in free end 244, adjacent to intermediate portion 245, to facilitate severance of the tab and removal of the diaper from the infant.

The refastened diaper is provided with a strong adhesive securement because of adhesive coating 250 on free working end 244. The strength of the adhesive permits many openings and closures of the diaper.

According to a further aspect of this invention, adhesive tab fastener assemblies for securing two flaps or substrates together, such as opposite ends of a disposable diaper, can be preassembled before being secured to the diaper. Referring to FIG. 9, adhesive tab fastener assembly 300 comprises a backing web 330 having inner face 336, outer face 338 and adhesive coating 339 on inner face 336. Backing web 330 includes distal end portion 378 and major portion 380 which carries release layer 352 on outer face 338 thereof.

Tab fastener assembly 300 further includes tape segment 340 which has pressure-sensitive adhesive coating 350 on inner face 346 and includes fixed end 342 adapted for attachment to one corner of the diaper inwardly of edge 382 of backing web 330, intermediate portion 345 which is permanently attached to backing web 330 along distal end portion 378 adjacent edge 382, and free working end 344 adhesive coating 350 of which is releasably attached to release layer 352 and is separable therefrom to make free working end 34 available for securement to the opposite corner of the diaper.

The pre-assembled tab fastener assembly 330 can be conveniently supplied in a roll. In such a case release properties can be imparted to outer face 348 of tape segment 340 to prevent permanent attachment of adhesive-coated inner face 346 of fixed end 342 and of adhesive-coated inner face 336 of backing web 330 to outer face 348 of tape segment 340 when the tab fastener is supplied in roll form. Alternatively, release liner 384 may be releasably attached to adhesive 350 carried on inner face 346 of fixed end 342 and to adhesive 339 carried on inner face 336 of backing web 330. Release liner 384 is removed prior to affixing tab fastener assembly 300 to the diaper.

Another embodiment of a pre-assembled tab fastener assembly is depicted in FIG. 10. Tab fastener assembly 400 is similar to the tab in the embodiment illustrated in FIGS. 5 and 6 and includes backing web 430 having adhesive coating 439 on inner face 436, and has an opposite outer face 438. The backing web includes distal end portion 478 adjacent edge 482, and remaining portion 480. Release means 470 is carried on outer face 438 of remaining portion 480 of backing web 430.

Tape segment 440 has a pressure-sensitive adhesive coating 450 on inner face 446 thereof, and has an opposite outer face 448. Fixed end 442 of tape segment 440 is adapted for attachment to one end of a diaper, intermediate portion 445 is permanently attached to backing web 430 along distal end portion 478, and free working end 444 is releasably attached to first release means 452.

Tab fastener assembly 400 further includes transferable tape ribbon 462 which has pressure-sensitive adhesive coating 464 on inner face 466 by means of which transferable tape ribbon 462 is carried on backing web 430, and has an opposite outer face 468 on which first release means 453 is provided. Second release means 470 on outer face 438 of the remaining portion 480 of backing web 430 is adapted for engagement with pressure-sensitive adhesive coating 464 on transferable tape ribbon 462. Transferable tape ribbon 462 is separable from second release means 470 to make the transferable tape ribbon available for use in securing the transferable tape ribbon to an opposite corner of the diaper to secure the diaper about an infant, and free working end 444 of tape segment 440 is separable from transferable tape ribbon 462 to enable a user to remove the diaper from the infant. The diaper can thereafter be refastened about the infant by means of a pressure-sensitive adhesive coating 450 on free end 444 of tape segment 440.

Transferable tape ribbon 462 includes fixed end 472 and grippable free end 474. Outer face 468 of fixed end 472 is coextensive with and is releasably attached to adhesive-coated inner face 446 of free working end 444 of tape segment 440, and free end 474 extends beyond edge 476 of tape segment 440.

In a manner similar to the embodiment shown in FIG. 9, tab fastener assembly 440 can be supplied as a roll suitably backsized with a release composition, or auxiliary release liner 484 can be provided and be releasably attached to adhesive-coated inner face 446 of fixed end 442 and adhesive-coated inner face 446 of backing web 430. Release liner 484 can be removed prior to positioning tab fastener assembly 400 on one corner of a diaper.

Referring to both embodiments of the pre-assembled tab fasteners, distal end portion 378, 478 which is adhesively attached to tape segment 340, 440 can be from about ¼ inch to about ⅜ inch in length to achieve the desired distribution of stresses imposed on tape segment 340, 440. Distal end portions 378 and 478 can also be longer or shorter, depending on the tape tab materials that are employed.

In all of the embodiments, the release means, such as release means 52 in FIG. 3, may comprise a ribbon segment or release strip having a release-coated surface which provides the release region, and an adhesive coating on the opposite face by means of which the release strip is anchored to facing anchoring leg 34. Alternatively, the release means may comprise a release layer which is a surface coating on outer fce 38 of facing anchoring leg 34, and preferably comprises a silicone release compound, or the like. The release strip or release layer preferably provides a release region of about the same width as tab 16 and is substantially coextensive with adhesive coating 50 on tape segment 40. However, the release region may have a greater width than tape segment 40 so as to provide for manufacturing tolerances.

It is also desirable to provide gripping means as shown in FIG. 8, to facilitate separation of transferable tape ribbon 262 from backing web 230, and for separating tape segment 240 from transferable tape ribbon 262. Thus, free end 244 of tape segment 240 and grippable portion 274 of transferable tape ribbon 262, respectively, can be provided with projecting portions 280 and 282 which extend beyond outermost edges 290 and 292 of adhesive coatings 250 and 264, whereby outwardly extending portions 294 and 296 provide gripping means.

Adhesive tabs suitable for the purposes of the present invention can be made from a wide variety of materials, provided that such materials are sufficiently flexible. Preferred materials for this purpose are polyolefin webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coatings 50 and 264 are provided by applying a coat of a pressure-sensitive adhesive composition known in the art to be the appropriate surfaces of tape segment 40 and transferable tape ribbon 262. The applied adhesive shall have good track, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, non-woven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous non-woven starting web into positions surrounding less dense fabric portions by passage of a fluid through the starting material. The fibers within the groupings are mechanically interlocked, and may be arranged into various patterns, as is well known to those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a nonapertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling the free end of the tab away from its temporary engagement with the release surface of backing web 30 to expose the adhesive on the free end of the tab. The tabs are then used to secure the diaper in the desired position by simply urging the pressure-sensitive adhesive surfaces in contact with the adjacent outer surface of the diaper. Where the tabs include transferable tape ribbon 262, the tabs can be detached and refastened as described hereinabove. The applied diaper assumes the configuration illustrated in FIG. 4.

The foregoing description and the drawing are illustrative but are not to be taken as limiting. Still other variations and modifications are possible without departing from the spirit and scope of the present invention.

I claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:
   a backing web folded over to form first and second anchoring legs each having an inner face and an outer face and receiving a marginal portion of the diaper therebetween, said inner face of said anchoring legs being provided with an adhesive coating by means of which said first anchoring leg is permanently attached to a marginal portion of said backing sheet and said second anchoring leg is permanently attached to a marginal portion of said facing sheet;
   a securing tape segment having an inner face and an outer face and including a fixed end permanently attached to said backing sheet inwardly of said first anchoring leg, a free working end provided with a pressure-sensitive adhesive coating on said inner face thereof, and an intermediate portion of said tape segment between said fixed end and said free working end permanently attached to the outer face of said first anchoring leg;
   release means associated with said tab fastener means and releasably attached to said adhesive coating on said free working end;
   said free working end being separable from said release means to make said free working end available for securing said diaper about an infant.

2. The disposable diaper as defined in claim 1 wherein an adhesive coating is provided on said inner face of said fixed end, wherein an adhesive coating is provided on said inner face of said intermediate portion, and wherein said adhesive coatings on said free working end, fixed end and intermediate portion comprise a continuous coating of pressure-sensitive adhesive on said inner face of said tape segment.

3. The disposable diaper as defined in claim 1 wherein said release means is carried on said backing web and includes a release portion on said outer face of said second anchoring leg which provides a release region substantially coextensive with said pressure-sensitive adhesive coating on said free working end; and wherein
   said free working end is movable from a folded-over storage position in which said free working end is releasably held by said release region to a working position in which said adhesive-coated free working end is available for use in securing said diaper about an infant.

4. The disposable diaper as defined in claim 3 wherein said first anchoring leg has a distal end segment and an opposite end segment which is situated between said second anchoring leg and said distal end segment, and wherein said release means includes a second release portion on said outer face of said opposite end segment of said first anchoring leg, said intermediate portion of said tape segment being permanently attached to said distal end segment of said first anchoring leg.

5. The disposable diaper as defined in claim 1 wherein said second anchoring leg is longer than said first anchoring leg.

6. The disposable diaper as defined in claim 1 wherein said release means is a release coating on said outer face of a portion of said backing web.

7. The disposable diaper as defined in claim 6 wherein each said release coating comprises a silicone release compound.

8. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:
   a backing web folded over to form first and second anchoring legs each having an inner face and an outer face and receiving a marginal portion of the diaper therebetween, said inner face of said anchoring legs being provided with an adhesive coating by means of which said first anchoring leg is permanently attached to a marginal portion of said backing sheet and said second anchoring leg is permanently attached to a marginal portion of said facing sheet;
   a securing tape segment having an inner face and an outer face and including a fixed end permanently attached to said backing sheet inwardly of said first anchoring leg, a free working end provided with a pressure-sensitive adhesive coating on said inner face thereof, and an intermediate portion of said tape segment between said fixed end and said free working end permanently attached to the outer face of said first anchoring leg;

a transferable tape ribbon removably attached to said free working end of said tape segment, having one face bearing a pressure-sensitive adhesive coating, and an opposite face; and release means for releasable engagement with said pressure-sensitive adhesive coating on said transferable tape ribbon;

said free working end of said securing tape segment being removable from said transferable tape ribbon to enable said diaper to be opened and to make said pressure-sensitive adhesive coating on said free working end of said tape segment available for use in refastening said diaper about said infant.

9. The disposable diaper as defined in claim 8 wherein said release means is carried on said backing web and includes a release portion on said outer face of said second anchoring leg which provides a release region substantially coextensive with said pressure-sensitive adhesive coating on said transferable tape segment; and wherein said transferable tape ribbon is movable from a folded-over storage position in which said transferable tape ribbon is releasably adhered to said release region to an extended working position in which said pressure-sensitive adhesive coating on said transferable tape ribbon is available for use in securing said diaper about said infant.

10. The disposable diaper as defined in claim 8 wherein said transferable tape ribbon has a fixed portion and a grippable portion, one face of said fixed portion being coextensive with but removably attached to said adhesive-coated face of said free working end, and the grippable portion extending beyond the free working end of said tape segment.

11. The disposable diaper as defined in claim 8 wherein said release means is a release coating on said outer face of a portion of said backing web.

12. The disposable diaper as defined in claim 8 wherein said opposite face has not only sufficient release properties to permit separation of said free working end therefrom for diaper inspection or removal but also sufficient holding properties to maintain diaper securement.

13. An adhesive tab fastener assembly for securing two flaps together, comprising:

a first flap with an inside surface and an outside surface, a backing web having an inner face and an outer face, said inner face being provided with an adhesive coating for attachment of said backing web to a marginal portion of the first flap, said backing web including a distal end portion along one end thereof, for attachment to the outside surface of the first flap, and a remainder portion carrying release means on the outer face thereof for attachment to the marginal portion of the first flap on at least the inside surface thereof;

a securing tape segment having an inner face and an outer face, a pressure-sensitive adhesive coating being provided on the inner face thereof, said tape segment further including a fixed end adapted for attachment to said first flap inwardly of said backing web, an intermediate portion permanently attached to said backing web at the distal end of said backing web, and a free working end releasably attached to said release means, said free working end being separable from said first release means to make said free working end available for securement to the other of said flaps.

14. The adhesive tab fastener assembly as defined in claim 13 wherein said release means is a release coating on the outer face of said remainder portion.

15. An adhesive tab fastener assembly as defined in claim 13 further including release liner means releasably attached to said adhesive-coated inner face of said fixed end of said tape segment and to said adhesive-coated inner face of said backing web.

16. The adhesive tab fastener assembly as defined in claim 13 further including a transferable tape ribbon having an inner face and an outer face, said transferable tape ribbon having a pressure-sensitive adhesive coating on the inner face thereof by means of which said transferable tape ribbon is releasably attached to said backing web and a second release means on the outer face of said transferable tape ribbon, said transferable tape ribbon being separable from said release means to make said transferable tape ribbon available for use in securing said transferable tape ribbon to the other of said flaps, and said free working end of said securing tape segment being separably attached to said release means to make said pressure-sensitive adhesive coating on said free working end available for use in refastening said tab fastener to the other of said flaps.

17. The adhesive tab fastener assembly as defined in claim 16, wherein said transferable tape ribbon has a fixed portion and a grippable portion, one face of said fixed portion being coextensive with but removably attached to said adhesive-coated face of said free working end, and the grippable portion extending beyond the free working end of said tape segment.

* * * * *